(12) United States Patent
Suk et al.

(10) Patent No.: US 12,307,661 B2
(45) Date of Patent: May 20, 2025

(54) METHOD AND APPARATUS FOR REASONING AND REINFORCING DECISION IN BRAIN DISEASE DIAGNOSIS MODEL

(71) Applicant: KOREA UNIVERSITY RESEARCH AND BUSINESS FOUNDATION, Seoul (KR)

(72) Inventors: Heung-Il Suk, Seoul (KR); Kwan Seok Oh, Seoul (KR)

(73) Assignee: Korea University Research and Business Foundation, Seoul (KR)

(*) Notice: Subject to any disclaimer, the term of this patent is extended or adjusted under 35 U.S.C. 154(b) by 520 days.

(21) Appl. No.: 17/714,390

(22) Filed: Apr. 6, 2022

(65) Prior Publication Data
US 2023/0162350 A1 May 25, 2023

(30) Foreign Application Priority Data
Nov. 24, 2021 (KR) .................. 10-2021-0163276

(51) Int. Cl.
| | |
|---|---|
| *G06T 7/00* | (2017.01) |
| *A61B 5/00* | (2006.01) |
| *A61B 5/055* | (2006.01) |
| *G06V 10/40* | (2022.01) |
| *G06V 10/764* | (2022.01) |
| *G16H 30/40* | (2018.01) |
| *G16H 50/20* | (2018.01) |

(52) U.S. Cl.
CPC .......... *G06T 7/0012* (2013.01); *A61B 5/0042* (2013.01); *A61B 5/055* (2013.01); *A61B 5/7267* (2013.01); *G06V 10/40* (2022.01); *G06V 10/764* (2022.01); *G16H 30/40* (2018.01); *G16H 50/20* (2018.01); *G06T 2207/10088* (2013.01); *G06T 2207/20081* (2013.01); *G06T 2207/30016* (2013.01)

(58) Field of Classification Search
CPC ......... G06T 7/0012; G06T 2207/10088; G06T 2207/20081; G06T 2207/30016; A61B 5/0042; A61B 5/055; A61B 5/7267; G06V 10/40; G06V 10/764; G16H 30/40; G16H 50/20
See application file for complete search history.

(56) References Cited

FOREIGN PATENT DOCUMENTS
KR 10-2021-0105724 A 8/2021

OTHER PUBLICATIONS

C. Lian, M. Liu, Y. Pan and D. Shen, "Attention-Guided Hybrid Network for Dementia Diagnosis With Structural MR Images," in IEEE Transactions on Cybernetics, vol. 52, No. 4, pp. 1992-2003, Jul. 28, 2020, doi: 10.1109/TCYB.2020.3005859. (Year: 2020).*
Oh, Kwanseok, et al. "Born Identity Network: Multi-way Counterfactual Map Generation to Explain a Classifier's Decision." arXiv: 2011. 10381v4, Nov. 20, 2020. (Year: 2020).*
(Continued)

*Primary Examiner* — Sean M Conner
*Assistant Examiner* — Renae A Bitor
(74) *Attorney, Agent, or Firm* — NSIP Law (57) ABSTRACT

Disclosed are a method and an apparatus for reasoning and reinforcing a decision in a brain disease diagnosis model.

8 Claims, 6 Drawing Sheets

(56) References Cited

OTHER PUBLICATIONS

Lian, C., Liu, M., Zhang, J., & Shen, D. (2018). Hierarchical fully convolutional network for joint atrophy localization and Alzheimer's disease diagnosis using structural MRI. IEEE transactions on pattern analysis and machine intelligence, 42(4), 880-893. (Year: 2018).*

Oh, Kwanseok, et al. "Born Identity Network: Multi-way Counterfactual Map Generation to Explain a Classifier's Decision." arXiv:2011.10381v4, Apr. 8, 2021, (17 pages in English).

* cited by examiner

METHOD AND APPARATUS FOR REASONING AND REINFORCING DECISION IN BRAIN DISEASE DIAGNOSIS MODEL

CROSS-REFERENCE TO RELATED APPLICATION

This application claims under 35 U.S.C. § 119(a) the benefit of Korean Patent Application No. 10-2021-0163276 filed on Nov. 24, 2021, the entire contents of which are incorporated herein by reference.

BACKGROUND

(a) Technical Field

The present disclosure relates to a method and an apparatus for reasoning and reinforcing decision in a brain disease diagnosis model, and more particularly, to a method and an apparatus for not only providing a counterfactual map capable of inferring a decision reason of a brain disease diagnosis model in an explainable AI field, but also improving diagnosis performance using the provided counterfactual map as a guidance of the model.

(b) Background Art

Explainable artificial intelligence (XAI) is a method for explaining decisions or answers made by artificial intelligence in a form that the human can understand, by the artificial intelligence itself, so that transparency and reliability can be secured by analyzing a causal relationship in decision-making to provide appropriate grounds to users.

In particular, as deep learning derives superior performance in the medical field, research has been actively conducted along with the demands for interpretability and explainability corresponding thereto.

However, achieving both interpretability and high performance for decision-making is still an unresolved problem even in the XAI field because a trade-off problem is accompanied.

To this end, various studies have been conducted to interpret the model by applying heuristic or perturbation to a gradient-based method or input using back propagation from a pre-learned model, but not only there is a limit to derive fundamental explainability for analyzing diagnostic results, but also there is a problem of interpretation that is difficult to be understood unless you are an expert.

Therefore, a counterfactual reasoning method, which can explain the decision of the model in a virtual situation that is essentially similar to a method of processing knowledge by humans, is attracting attention as an excellent technique to provide an explanation that is closest to the level of human knowledge.

In general, there are used adversarial learning through a generative model used in the counterfactual reasoning method, and image to image translation to maintain identity to the input, and a condition method of providing a decisive guidance to allow a constructor to better generate class-specific samples.

However, a method for reasoning and reinforcing the decision in the brain disease diagnosis model through counterfactual reasoning has not yet been specifically presented.

SUMMARY OF THE DISCLOSURE

In order to solve the problem of the related art, an object of the present disclosure is to provide a method and an apparatus for reasoning and reinforcing a decision in a brain disease diagnosis model capable of providing a reason to allow a user to analyze a causal relationship through a counterfactual reasoning method, and improving the performance of a diagnosis model by using a counterfactual map by considering both local and global sparse information while presenting a method for deriving explainability similar to that of human knowledge.

According to an aspect of the present disclosure, there is provided an apparatus for reasoning and reinforcing a decision in a diagnosis model including a processor; and a memory connected to the processor, wherein the memory stores program instructions executable by the processor to generate a counterfactual map for an input image by giving one of a plurality of target labels to a first feature map extracted for the input image included in a dataset by a counterfactual map generator, generate a target image by linear-summing the input image and the counterfactual map, classify an attribute of the target image by extracting a second feature map of the target image by a diagnosis model, perform the learning of the counterfactual map generator and the diagnosis model by a discriminator that receives one of the dataset as real data and the target image as virtual data to output a probability value, and reinforce the diagnosis model by learning an attention module concatenated to a feature extractor extracting a second feature map of the diagnosis module by using the learned counterfactual map generator as a guidance map generator.

The dataset may consist of brain magnetic resonance images, and the diagnosis model may be a model for diagnosing brain disease.

The feature extractor may consist of a plurality of convolutional layers, and the attention module may extract an attended feature map for a first input image by referring to a guidance map output from the guidance map generator capable of guiding a structural change occurrence region of the brain due to brain disease with respect to the feature map output by each of the plurality of convolutional layers for the first input image.

The attention module may include a local attention module, a contextual attention module, and a global attention module, and generate an attention mask by multiplying the output results of the local attention module and the contextual attention module for each element and multiplying the output results of the global attention module and the contextual attention module for each element to extract an attended feature map for the first input image.

The diagnosis module may classify a class of the first input image by inputting the attended feature map.

The guidance map generator may generate the guidance map by giving target labels corresponding to normal and abnormal with respect to the extracted feature map to the first input image.

After the learning of the attention module is completed, the learned attention module may be concatenated to the counterfactual map generator and the feature extractor of the guidance map generator.

According to another aspect of the present disclosure, there is provided a method for reasoning and reinforcing a decision in a diagnosis model in an apparatus including a process and a memory, the method including steps of: generating, by a counterfactual map generator, a counterfactual map for an input image by giving one of a plurality of target labels to a first feature map extracted for the input image included in a dataset; generating a target image by linear-summing the input image and the counterfactual map; classifying, by a diagnosis model, an attribute of the target image by extracting a second feature map of the target image; performing the learning of the counterfactual map generator and the diagnosis model by a discriminator that receives one of the dataset as real data and the target image as virtual data to output a probability value; and reinforcing the diagnosis model by learning an attention module concatenated to a feature extractor extracting a second feature map of the diagnosis module by using the learned counterfactual map generator as a guidance map generator.

According to yet another aspect of the present disclosure, there is provided a computer-readable recording medium storing a program for performing the method.

According to the present disclosure, by utilizing the generative model to which the condition method is applied, there is an advantage of being applied not only to a single or binary diagnosis model, but also to a diagnosis model dealing with multiple classes, and providing interpretability of a human knowledge level capable of supporting diagnostic performance to end users through a counterfactual map.

In addition, according to the present disclosure, there is an advantage of improving the performance of a diagnosis model through fine tuning by using a counterfactual map as one data augmentation.

Furthermore, there is an advantage of using a counterfactual map as a guidance for improving the performance of the diagnosis model while proposing an attention module capable of considering both local and global scarce information and repeatedly performing providing diagnostic explanation and improving diagnostic performance by the model itself to improve complementarily results of both techniques.

DETAILED DESCRIPTION

The present disclosure may make various modifications and have various embodiments, and specific embodiments will be illustrated in the drawings and will be described in detail.

However, the present disclosure is not limited to specific embodiments, and it should be understood that the present disclosure covers all modifications, equivalents and replacements included within the idea and technical scope of the present disclosure.

The present embodiment provides a method for inducing counterfactual reasoning and improving diagnostic performance for decision-making in a diagnosis model.

Figure 1:
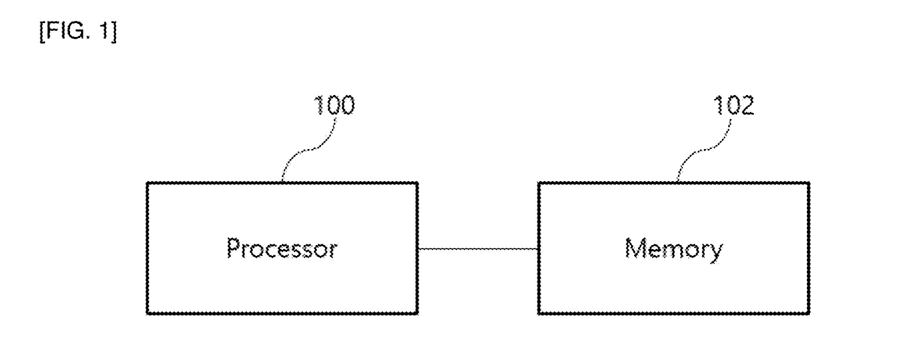
FIG. 1 is a diagram illustrating a configuration of an apparatus for reasoning and reinforcing a decision in a diagnosis model according to the present embodiment.

FIG. 1 is a diagram illustrating a configuration of an apparatus for reasoning and reinforcing a decision in a diagnosis model according to the present embodiment.

As illustrated in FIG. 1, the apparatus according to the present embodiment may include a processor 100 and a memory 102.

The processor 100 may include a central processing unit (CPU) capable of executing a computer program, other virtual machines, or the like.

The memory 102 may include a nonvolatile storage device such as a fixed hard drive or a detachable storage device. The detachable storage device may include a compact flash unit, a USB memory stick, etc. The memory 102 may also include volatile memories such as various types of random access memories.

The memory 102 according to the present embodiment stores program instructions for reasoning and reinforcing a decision in a diagnosis model, in particular, a brain disease diagnosis model.

The program instructions according to the present embodiment generates a counterfactual map for an input image by giving one of a plurality of target labels to a first feature map extracted for the input image included in a dataset by a counterfactual map generator, generates a target image by linear-summing the input image and the counterfactual map, classifies an attribute of the target image by extracting a second feature map of the target image by a diagnosis model, performs the learning of the counterfactual map generator and the diagnosis model by a discriminator that receives one of the dataset as real data and the target image as virtual data to output a probability value, and reinforces the diagnosis model by learning an attention module concatenated to a feature extractor extracting a second feature map of the diagnosis module by using the learned counterfactual map generator as a guidance map generator.

Here, the dataset may be brain magnetic resonance images for diagnosing brain disease.

Hereinafter, a diagnosis model for diagnosing brain disease will be mainly described, but the present embodiment is not limited thereto, and the present embodiment may also be applied to a case of reasoning and reinforcing a model for classification even in various types of medical data and computer vision fields.

According to the present embodiment, a feature extractor and a classifier included in the diagnosis model are learned through a counterfactual map and a discriminator, and then, an attention module capable of considering both local and global regions and a guidance map capable of guiding an area where structural changes in the brain occur due to brain disease are used to improve the performance of the diagnosis module.

Hereinafter, the diagnosis model, the counterfactual map, and the attention module will be described in detail with reference to the drawings.

Figure 2:
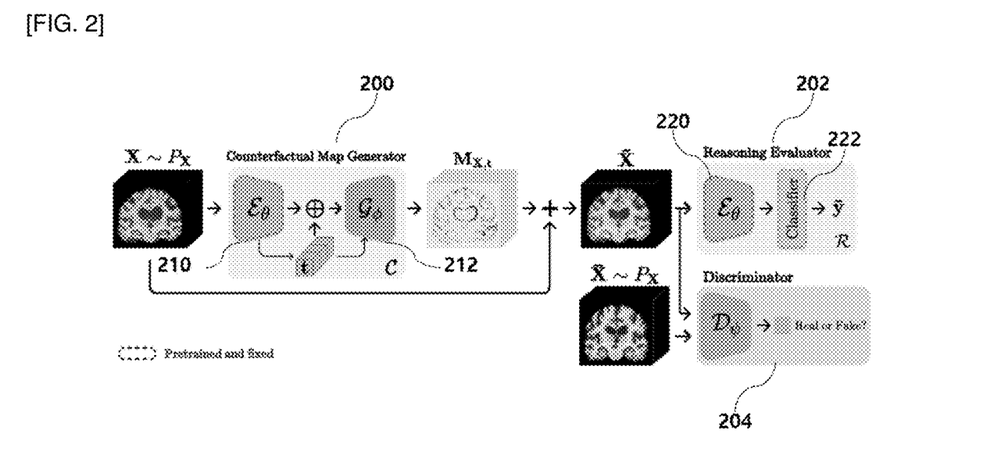
FIG. 2 is a diagram illustrating a system for diagnosing brain disease through a counterfactual map according to the present embodiment.

FIG. 2 is a diagram illustrating a system for diagnosing brain disease through a counterfactual map according to the present embodiment.

As illustrated in FIG. 2, the system according to the present embodiment includes a counterfactual map generator 200, a reasoning evaluator 202, and a discriminator 204.

The counterfactual map generator 200 may include a first feature extractor 210 and a map generator 212.

The first feature extractor 210 may be an encoder including a plurality of convolutional layers, and extracts a first feature map of input images X~$P_X$ included in a brain magnetic resonance image dataset.

The extracted first feature map is given with a target label t and input to the map generator 212, and the map generator 212 generates a counterfactual map ($M_{X,t}$) for the first feature map to which the target label is given.

Here, the counterfactual map is data to which the anatomical or morphological meaning of brain disease is given.

Figure 3:
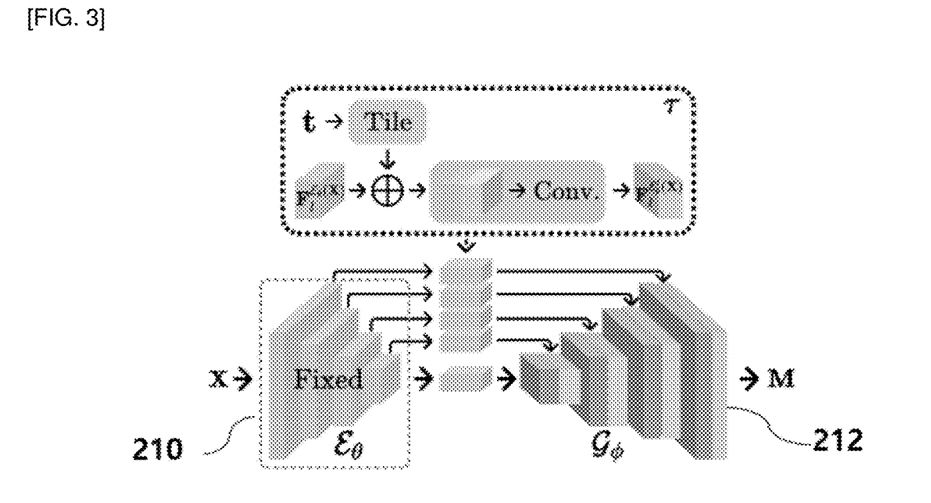
FIG. 3 is a diagram illustrating in detail a process of generating a counterfactual map according to the present embodiment.

FIG. 3 is a diagram illustrating in detail a process of generating a counterfactual map according to the present embodiment.

As illustrated in FIG. 3, the target label t is tiled and concatenated for each channel through a skip connection to generate a counterfactual map for an arbitrary target condition.

A target image $\tilde{X}$ is generated through a linear sum of the input image X and the counterfactual map ($M_{X,t}$), and the target image is defined as an image that enables the reasoning evaluator 202 to classify the target class with high reliability.

The discriminator 204 receives one of the dataset as real data $\overline{X}$~$P_X$, receives a target image as virtual data, and outputs a probability value.

The discriminator 204 discriminates whether the target image is real or fake.

As illustrated in FIG. 2, the reasoning evaluator 202 according to the present embodiment corresponds to a diagnosis model for diagnosing brain disease, and may include a second feature extractor 220 for extracting a second feature map for the target image and a classifier 222 for classifying the class of the target image.

According to the present embodiment, the reasoning evaluator 202 visualizes counterfactual reasoning capable of providing users with reliability and explainability for decision-making through adversarial learning and cycle consistency, and, as described above, performs the learning of the counterfactual map generator and the diagnosis model by repeatedly performing generation of the counterfactual map and the classification of the target class for various input images.

As such, after the learning of the counterfactual map generator and the diagnosis model is performed, the attention module for reinforcing the performance of the diagnosis model is applied.

Figure 4:
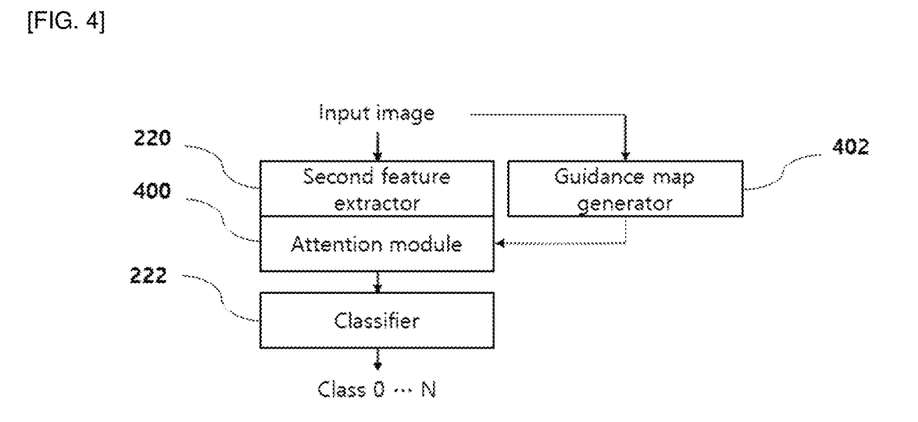
FIG. 4 is a diagram illustrating a configuration of a system for reinforcing a diagnosis model to which an attention module is applied according to the present embodiment.

FIG. 4 is a diagram illustrating a configuration of a system for reinforcing a diagnosis model to which an attention module is applied according to the present embodiment.

As illustrated in FIG. 4, the system for reinforcing the diagnosis model according to the present embodiment may be defined by adding an attention module 400 capable of considering both local and global regions and a guidance map generator 402 capable of guiding an area where structural changes of the brain occur due to brain disease to the second feature extractor 220 and the classifier 222 of the reasoning evaluator 202.

Figure 5:
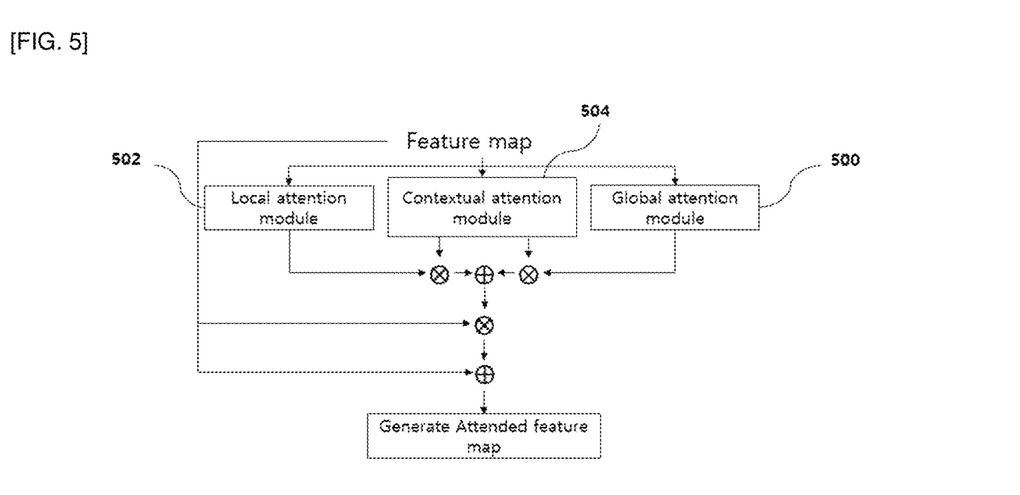
FIG. 5 is a diagram illustrating a detailed configuration of the attention module according to the present embodiment.
Figure 6:
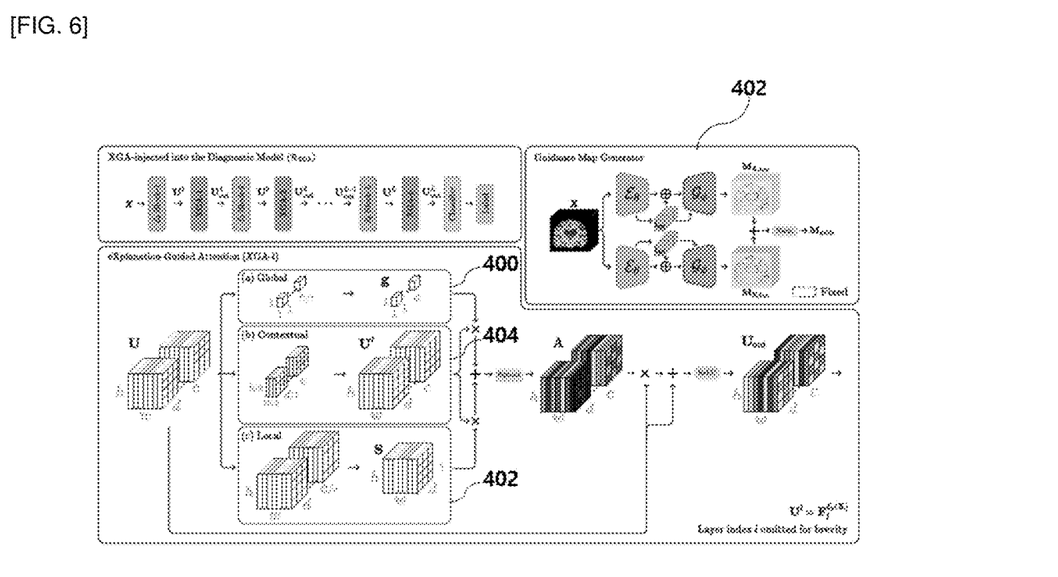
FIG. 6 is a diagram illustrating a detailed configuration of the system for reinforcing the diagnosis model to which the attention module is applied.

FIG. 5 is a diagram illustrating a detailed configuration of the attention module according to the present embodiment and FIG. 6 is a diagram illustrating a detailed configuration of the system for reinforcing the diagnosis model to which the attention module is applied.

As illustrated in FIGS. 5 to 6, the attention module 400 according to the present embodiment is an explanation-guided attention (XGA) that enhances an area sensitive to brain disease diagnosis and inhibits other areas, and may include a global attention module 500, a local attention module 502, and a contextual attention module 504.

In each of the attention modules 500 to 504 according to the present embodiment, feature maps $U^1$ to $U^L$ extracted from individual convolutional layers Block-L of the second feature extractor 220 consisting of a plurality of convolutional layers (L layers) are input, and provided as the number L corresponding to the individual convolutional layers.

The global attention module 500 calculates a global feature vector g in the feature map input using a squeeze-and-excitation method.

The local attention module 502 calculates a local feature attention map s in consideration of a local saliency component in the input feature map.

The contextual attention module 504 expands a field of view through dilated convolution so as to use relational information from a wider reception field, and outputs U' through non-linear transformation.

The outputs of the global attention module 500 and the contextual attention module 504 are multiplied for each element, and the outputs of the local attention module 502 and the contextual attention module 504 are multiplied for each element, and then the multiplied results are summed to output an attention mask A.

The attention mask A performs the excitation and inhibition of the input feature map U using a skip connection.

As illustrated in FIG. 6, a final output (attended feature map, $U_{out}$) is generated through element-wise product and linear sum of the input feature map and the attention mask.

Figure 7:
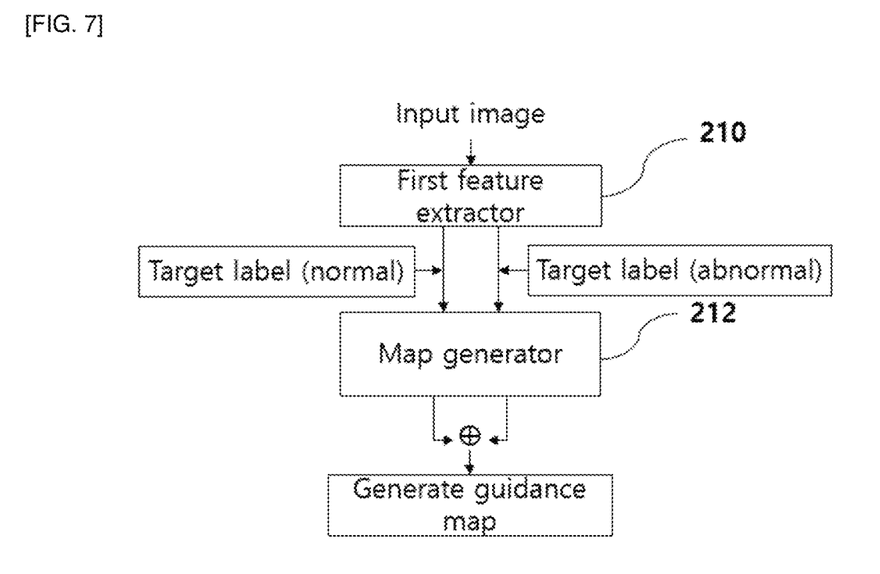
FIG. 7 is a diagram illustrating a detailed configuration of a guidance map generator according to the present embodiment.

FIG. 7 is a diagram illustrating a detailed configuration of a guidance map generator according to the present embodiment.

As illustrated in FIG. 7, the guidance map generator 402 includes a first feature extractor 210 and a map generator 212 like the counterfactual map generator 200 of FIG. 2.

However, only a target label corresponding to normal and a target label corresponding to abnormal in relation to brain disease are given to the feature map extracted by the first feature extractor 210 of the guidance map generator 402, and the map generator 212 generates a guidance map for the feature map to which the normal and abnormal target labels are given.

The guidance map generated as described above is input to the attention module 400, and the attention module 400 outputs an attended feature map.

Referring back to FIG. 4, the classifier 222 according to the present embodiment classifies a class of the input image by inputting the attended feature map.

Figure 8:
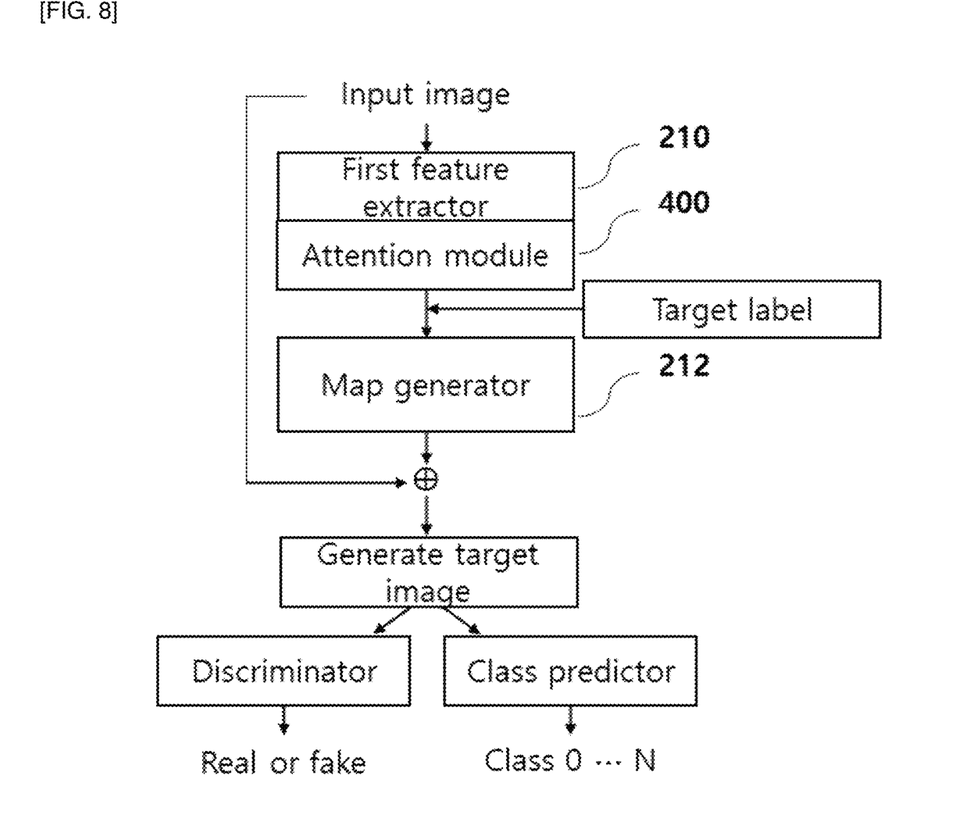
FIGS. 8 to 9 are diagrams illustrating configurations of a counterfactual map generator and a guidance map generator to which the attention module is applied.
Figure 9:
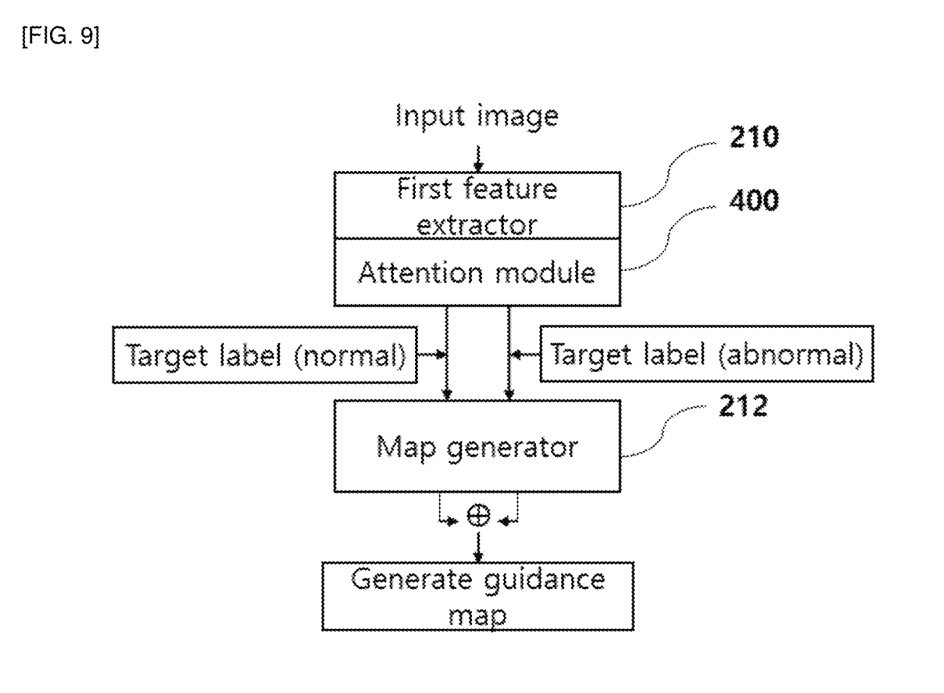

FIGS. 8 to 9 are diagrams illustrating configurations of a counterfactual map generator and a guidance map generator to which the attention module is applied.

After the learning of the attention module is completed through the network configuration as illustrated in FIG. 6, the learned attention module is concatenated to the counterfactual map generator 200 and the first feature extractor 210 of the guidance map generator 402 to output the attended feature map, and as a result, generate a counterfactual map and a guidance map, thereby further reinforcing the performance of the diagnosis model.

The embodiments of the present disclosure described above are disclosed for purposes of illustration, and it will be apparent to those skilled in the art that various modifications, additions, and substitutions are possible within the spirit and scope of the present disclosure and these modifications, changes, and additions should be considered as falling within the scope of the following claims.

What is claimed is:

1. An apparatus for reasoning and reinforcing a decision in a diagnosis model, the apparatus comprising:
a processor; and
a memory connected to the processor,
wherein the memory stores program instructions executable by the processor to generate a counterfactual map for an input image by giving one of a plurality of target labels to a first feature map extracted for the input image included in a dataset by a counterfactual map generator,
generate a target image by linear-summing the input image and the counterfactual map,
classify an attribute of the target image by extracting a second feature map of the target image by a diagnosis model,
train the counterfactual map generator and the diagnosis model by a discriminator that receives one of the dataset as real data and the target image as virtual data to output a probability value, and
reinforce the diagnosis model by training an attention module concatenated to a feature extractor extracting a second feature map of the diagnosis model by using the trained counterfactual map generator as a guidance map generator,
wherein the dataset consists of brain magnetic resonance images and the diagnosis model is a model for diagnosing brain disease,
wherein the feature extractor consists of a plurality of convolutional layers,
wherein the attention module extracts an attended feature map for a first input image by referring to a guidance map output from the guidance map generator capable of guiding a structural change occurrence region of the brain due to brain disease with respect to the feature map output by each of the plurality of convolutional layers for the first input image,
wherein the attention module includes a local attention module, a contextual attention module, and a global attention module, and generates an attention mask by multiplying output results of the local attention module and the contextual attention module for each element and multiplying output results of the global attention module and the contextual attention module for each element to extract an attended feature map for the first input image, and
wherein the diagnosis model classifies a class of the first input image by inputting the attended feature map.

2. The apparatus of claim 1, wherein the guidance map generator generates the guidance map by giving target labels corresponding to normal and abnormal with respect to the extracted feature map to the first input image.

3. The apparatus of claim 2, wherein after the learning training of the attention module is completed, the trained attention module is configured to be concatenated to the counterfactual map generator and the feature extractor of the guidance map generator.

4. A method for reasoning and reinforcing a decision in a diagnosis model in an apparatus including a process and a memory, the method comprising steps of:
generating, by a counterfactual map generator, a counterfactual map for an input image by giving one of a plurality of target labels to a first feature map extracted for the input image included in a dataset;
generating a target image by linear-summing the input image and the counterfactual map;
classifying, by a diagnosis model, an attribute of the target image by extracting a second feature map of the target image;
training the counterfactual map generator and the diagnosis model by a discriminator that receives one of the dataset as real data and the target image as virtual data to output a probability value; and
reinforcing the diagnosis model by training an attention module concatenated to a feature extractor extracting a second feature map of the diagnosis model by using the trained counterfactual map generator as a guidance map generator,
wherein the dataset consists of brain magnetic resonance images and the diagnosis model is a model for diagnosing brain disease,
wherein the feature extractor consists of a plurality of convolutional layers,
wherein the attention module extracts an attended feature map for a first input image by referring to a guidance map output from the guidance map generator capable of guiding a structural change occurrence region of the brain due to brain disease with respect to the feature map output by each of the plurality of convolutional layers for the first input image,
wherein the attention module includes a local attention module, a contextual attention module, and a global attention module, and generates an attention mask by multiplying output results of the local attention module and the contextual attention module for each element and multiplying output results of the global attention module and the contextual attention module for each element to extract an attended feature map for the first input image, and
wherein the diagnosis model classifies a class of the first input image by inputting the attended feature map.

5. A computer-readable recording medium storing a program for performing the method according to claim 4.

6. An apparatus for reasoning and reinforcing a decision in a diagnosis model, the apparatus comprising:
a processor; and
a memory connected to the processor,
wherein the memory stores program instructions executable by the processor to generate a counterfactual map for an input image by giving one of a plurality of target labels to a first feature map extracted for the input image included in a dataset by a counterfactual map generator,
generate a target image by linear-summing the input image and the counterfactual map,
classify an attribute of the target image by extracting a second feature map of the target image by a diagnosis model,
train the counterfactual map generator and the diagnosis model by a discriminator that receives one of the dataset as real data and the target image as virtual data to output a probability value, and
reinforce the diagnosis model by training an attention module concatenated to a feature extractor extracting a second feature map of the diagnosis model by using the trained counterfactual map generator as a guidance map generator,
wherein the dataset consists of brain magnetic resonance images and the diagnosis model is a model for diagnosing brain disease,
wherein the feature extractor consists of a plurality of convolutional layers, wherein the attention module extracts an attended feature map for a first input image by referring to a guidance map output from the guidance map generator capable of guiding a structural change occurrence region of the brain due to brain disease with respect to the feature map output by each of the plurality of convolutional layers for the first input image, and wherein the guidance map generator generates the guidance map by giving target labels corresponding to normal and abnormal with respect to the extracted feature map to the first input image, and wherein after the training of the attention module is completed, the trained attention module is configured to be concatenated to the counterfactual map generator and the feature extractor of the guidance map generator.

7. The apparatus of claim 6, wherein the attention module includes a local attention module, a contextual attention module, and a global attention module, and generates an attention mask by multiplying output results of the local attention module and the contextual attention module for each element and multiplying output results of the global attention module and the contextual attention module for each element to extract an attended feature map for the first input image.

8. The apparatus of claim 7, wherein the diagnosis model classifies a class of the first input image by inputting the attended feature map.

* * * * *